United States Patent [19]

Karbach et al.

[11] Patent Number: 4,906,652
[45] Date of Patent: Mar. 6, 1990

[54] AZOLYMETHYLOXIRANES AND THEIR USE AS CROP PROTECTION AGENTS

[75] Inventors: Stefan Karbach; Bernd Janssen, both of Ludwigshafen; Norbert Meyer, Ladenburg; Hubert Sauter, Mannheim; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 183,448

[22] Filed: Apr. 14, 1988

Related U.S. Application Data

[63] Continuation of Ser. No. 839,163, Mar. 13, 1986, abandoned.

[30] Foreign Application Priority Data

Mar. 29, 1985 [DE] Fed. Rep. of Germany ....... 3511411
Oct. 12, 1985 [DE] Fed. Rep. of Germany ....... 3536529

[51] Int. Cl.⁴ .................. A01N 43/653; A01N 43/50; C07D 405/06
[52] U.S. Cl. ...................................: 514/383; 514/184; 514/399; 548/101; 548/341; 548/268.8
[58] Field of Search ....................... 514/184, 383, 399; 548/101, 262, 341

[56] References Cited

U.S. PATENT DOCUMENTS 4,464,381  8/1974  Janssen et al. ....................... 548/262
4,595,406  6/1986  Parry et al. ............................. 11/92

Primary Examiner—Glennon H. Hollrah
Assistant Examiner—Patricia L. Morris
Attorney, Agent, or Firm—Keil & Weinkauf

[57] ABSTRACT

Compounds of the formula

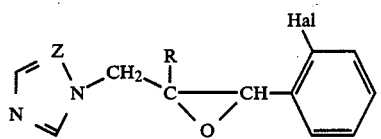

where R, Hal and Z have the meanings given in the disclosure. The compounds are suitable for use as fungicides.

7 Claims, No Drawings

AZOLYMETHYLOXIRANES AND THEIR USE AS CROP PROTECTION AGENTS

This application is a continuation of application Ser. No. 839,163, filed on Mar. 13, 1986 now abandoned.

The present invention relates to novel azole compounds, processes for their preparation, and fungicides containing these compounds.

European Patent 94,564 discloses azole compounds, in particular 2-(1,2,4-triazol-1-ylemthyl)-2-(4-chlorophenyl)-3-(2,4-dichlorophenyl)-oxirane, whose fungicidal action is not satisfactory in all cases.

We have found that compounds of the formula I

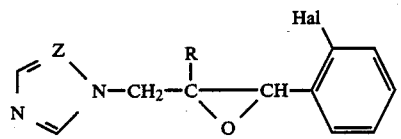

where R is $C_1$-$C_4$-alkyl, naphthyl, biphenyl or phenyl, and the phenyl radical may be substituted by halogen, nitro or phenoxy or by alkyl, alkoxy or haloalkyl, each of 1 to 4 carbon atoms, Hal is fluorine, chlorine or bromine and =Z— is =CH— or =N—, and their plant-tolerated addition salts with acids and metal salts possess a better fungicidal action than the known azole compounds, in particular against cereal diseases.

Compounds of the formula I contain chiral centers and are generaly obtained in the form of racemates or as diastereomer mixtures of erythro and threo forms. The erythro and threodiastereomers of the novel compounds can be separated in a conventional manner, for example by utilizing their different solubilities or by means of column chromatography, and can be isolated in pure form. the pure enantiomers can be obtained from such pure diastereomer pairs by conventional methods. Both the pure diastereomers or enantiomers and the mixtures of these obtained in the synthesis can be used as fungicides.

R is, for example, methyl, ethyl, propyl, isopropyl, butyl, sec-butyl, isobutyl, tert-butyl, 1-naphthyl, 2-naphthyl, p-biphenyl, phenyl, 2-chlorophenyl, 3-chlorophenyl, 4-chlorophenyl, 4-fluorophenyl, 4-bromophenyl, 2,4-dichlorophenyl, 3,4-dichlorophenyl, 3,5-dichlorophenyl, 3-chloro-4-methylphenyl, 2-methOxyphenyl, 3-methoxyphenyl, 2,4-dimethoxyphenyl, 3,4-dimethoxyphenyl, 4-methoxyphenyl, 4-ethoxyphenyl, 4-tert-butoxyphenyl, 4-methylphenyl, 4-ethylphenyl, 4-isopropylphenyl, 4-tert-butylphenyl, 4-phenoxyphenyl, 3-phenoxyphenyl, 3-nitrophenyl, 4-nitrophenyl, 3-trifluoromethylphenyl, 4-trifluoromethylphenyl or 4-phenylsulfonylphenyl.

Examples of addition salts with acids are the hydrochlorides, bromides, sulfates, nitrates, phosphates, oxalates and dodecylbenzenesulfonates. The activity of the salts is attributable to the cation, and the anion is in general unimportant. The novel active ingredient salts are prepared by reacting the azolymethyloxiranes (I) with suitable acids.

Metal complexes of the active ingredients I or of their salts can be formed, for example, with copper, zinc, tin, manganese, iron, cobalt or nickel, by reacting the azolylmethyloxiranes with the corresponding metal salts.

The compounds of the formula I can be prepared, for example, by a method in which (a) an appropriate intermediate of the formula II

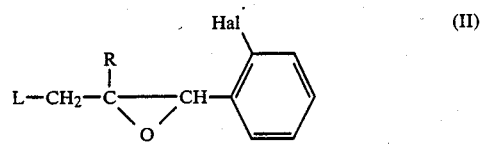

where L is a nucleophilically substituted leaving group, is reacted with an appropriate azole of the formula III

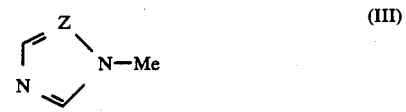

where Me is a hydrogen atom or a metal atom, or (b) a compound of the formula II where R and Hal have the above meanings and L is a hydroxyl group, is reacted with a compound of the formula IV.

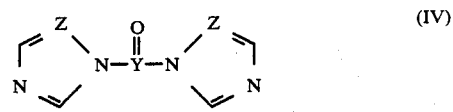

where Z has the stated meanings and Y is a carbon or sulfur atom, or (c) a compound of the formula V

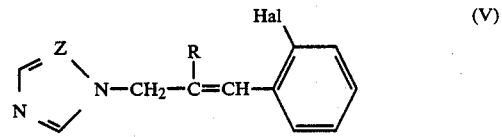

where Z, R and Hal have the stated meanings, is epoxidized, or (d) a compound of the formula VI

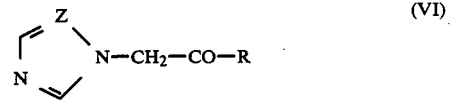

where Z and R have the stated meanings, is reacted with a compound of the general formula VII

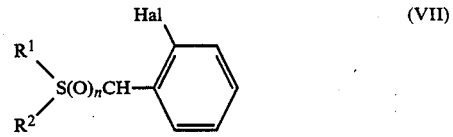

where hal has the stated meanings, $R^1$ and $R^2$ may be identical or different and are each methyl or phenyl, and n is zero or one, and, if required, the resulting compound is converted to its salts with physiologically tolerated acids.

Where Me is hydrogen, reaction (a) is carried out in the presence or absence of a solvent or diluent, with or without the addition of an inorganic or organic base and with or without the addition of a reaction acccelerator, at from 10° to 120° C. The preferred solvents or diluents include ketones, such as acetone, methyl ethyl ketone or cyclohexanone, nitriles, such as acetonitrile, esters, such as ethyl acetate, ethers, such as diethyl ether, tetrahydrofuran or dioxane, sulfoxides, such as dimethyl sulfoxide, amides, such as dimethylformamide, dimethylacetamide or N-methylpyrrolidone, sulfolane and mixtures of these.

Examples of suitable bases, which may also be used as acid acceptors in the reaction, are alkali metal hydroxides, such as lithium hydroxide, sodium hydroxide or potassium hydroxide, alkali metal carbonates, such as sodium carbonate, potassium carbonate, sodium bicarbonate or potassium bicarbonate, an excess of 1,2,4-triazole, pyridine and 4-dimethylaminopyridine. Other conventional bases may also be used.

Preferred reaction accelerators are metal halides, such as sodium iodide or potassium iodide, quaternary ammonium salts, such as tetrabutylammonium chloride, bromide or iodide, benzyltriethylammonium chloride or bromide, and crown ethers, such as 12-crown-4-, 15-crown-5, 18-crown-6, dibenzo-18-crown-6 or dicyclohexano-18-crown-6.

The reaction is carried out in general at from 20° to 150° C., under atmospheric or superatmospheric pressure, continuously or batchwise.

Where Me is a metal atom, reaction (a) is effected in the presence or absence of a solvent or diluent and with or without the addition of a strong inorganic or organic base, at from $-10°$ to 120° C. The preferred solvents or diluents include amides, such as dimethylformamide, diethylformamide, dimethylacetamide, diethylacetamide, N-methylpyrrolidone or hexamethylphosphorotriamide, sulfoxides, such as dimethyl sulfoxide, and finally sulfolane.

Examples of suitable bases, which may also be used as acid acceptors in the reaction, are alkali metal hydrides, such as lithium hydride, sodium hydride, potassium hydride, alkali metal amides such as sodium amide or potassium amide, and sodium tert-butoxide, potassium tert-butoxide, triphenylmethyl-lithium, -sodium and -potassium and naphthalene-lithium, -sodium and -potassium.

Suitable diluents for reaction (b) are polar organic solvents, such as nitriles, eg. acetonitrile, sulfoxides, eg. dimethyl sulfoxide, formamides, eg. dimethylformamide, ketones, eg. acetone, ethers, eg. diethyl ether or tetrahydrofuran, and in particular chlorohydrocarbons, eg. methylene chloride or chloroform.

In general, a temperature of from 0° to 100° C., preferably from 20° to 80° C., is employed. Where a solvent is present, the reaction is advantageously carried out at the boiling point of the particular solvent.

In carrying out process (b), about 1 mole of 1,1'-carbonylbis-1,2,4-triazole or 1,1'-carbonylbisimidazole or 1 mole of 1,1'-sulfonylbis-1,2,4-triazole or 1,1'-sulfonylbisimidazole is preferably employed per mole of the compound of the formula II (where L is OH), or 1,1'-sulfonylbis-1,2,4-triazole or 1,1'-sulfonylbisimidazole is produced in situ. To isolate the compounds of the formula I, the solvent is distilled off, the residue is taken up in an organic solvent, and the solution is washed with water.

The novel starting compounds II are obtained by epoxidation of the corresponding olefins IX:

$$L-CH_2-CR=CH-Hal \qquad (IX)$$

(cf. G. Dittus in Houben-Weyl-Müller, Methoden der organischen Chemie, Georg Thieme Verlag, Stuttgart, 1965, Vol. VI, 3, page 385 et seq.).

The compound IX is prepared by halogenating or oxidizing an olefin of the formula X $$H_3C-CA=CH-ortho-halogen\ phenyl \qquad (X)$$

in the allyl position by a conventional method.

Suitable halogenation reagents are N-chloro- and N-bromosuccinimide in a halohydrocarbon, such as carbon tetrachloride, trichloroethane or methylene chloride, at from 20° to 100° C. The allyl oxidation is carried out using a perester, such as tert-butyl perbenzoate or tert-butyl peracetate, in the presence of a heavy metal salt, eg. copper(I) chloride or copper(I) bromide, in an inert solvent at from 10° to 100° C.

The resulting allyl halides or allyl alcohols IX are then converted to the corresponding epoxides II (where L is halogen or OH). To do this, the olefins IX are oxidized with a peroxycarboxylic acid, such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid, in an inert solvent, preferably a chlorohydrocarbon, eg. methylene chloride, chloroform, carbon tetrachloride or dichloroethane, or, if appropriate, in acetic acid, ethyl acetate, acetone or dimethylformamide, in the presence or absence of a buffer, such as sodium acetate, sodium carbonate, sodium bicarbonate, disodium hydrogen phosphate or Triton B. The procedure is carried out at from 10° to 100° C. and, if necessary, the reaction is catalyzed, for example with iodine, sodium tungstate or light. The oxidation can also be carried out using an alkaline solution of hydrogen peroxide (about 30% strength) in methanol, ethanol, acetone or acetonitrile at from 25° to 30° C., or an alkyl hydroperoxide, eg. tert-butyl hydroperoxide, with the addition of a catalyst, eg. sodium tungstate, pertungstic acid, molybdenum-hexacarbonyl or vanadyl acetylacetonate. Some of the stated oxidizing agents can be produced in situ.

While the resulting epoxyhalides II (where L is halogen) can be reacted immediately according to process (a), the corresponding epoxyalcohols II (where L is OH) either can be reacted with a compound of the formula IV by process (b) or are converted to a reactive ester, which is then reacted with a compound III by process (a).

The reactive esters, which are reacted with III, are prepared by a conventional method (Houben-Weyl-Müller, Methoden der organischen Chemie, Georg Thieme Verlag, Stuttgart, 1955, volume 9, pages 388, 663 and 671). Examples of such esters are methanesulfonates, trifluoromethanesulfonates, 2,2,2-trifluoromethanesulfonates, nonafluorobutanesulfonates, 4-methylbenzenesulfonates, 4-bromobenzenesulfonates, 4-nitrobenzenesulfonates and benzenesulfonates.

The compounds X may be prepared by conventional processes for olefin synthesis (Houben-Weyl-Müller, Methoden der organischen Chemie, Georg Thieme Verlag, Stuttgart, 1972, volume V, 1b).

Process (c) is carried out similarly to the epoxidation of the compounds IX.

The starting compounds V are disclosed in German Laid-Open Application DOS 2,549,798 and can be prepared by the methods stated there.

For the novel process (d) azolyl ketones (eg. German Laid-Open Application DOS 2,063,857) of the formula VI, which are known from the literature, are reacted with sulfur derivatives of the formula VII.

The alkylidenesulfuranes VII (n=0) and oxisulfuranes VII (n=1) are prepared in situ by a conventional method (eg. H. O. House, Modern Synthetic Reactions, 2nd edition, ". W. Benjamin, Menlo Park 1972, page 712 et seq.), and are reacted with the azolyl ketones VI in an inert solvent, preferably an ether, such as diethyl ether, tetrahydrofuran or a mixture of the two, or in a hydrocarbon, such as pentane, hexane or a petroleum ether, at from −78° to 30° C.

The resulting compounds of the formula I are isolated by a conventional method, if necessary purified and, if desired, reacted with an acid to give a salt.

The Examples which follow illustrate the preparation of the active ingredients.

I. Preparation of the starting materials

EXAMPLE A 30 g of sodium methylate in 300 ml of dry methanol were introduced at 10° C. into a solution of 194.5 g of 2-chlorobenzyltriphenylphosphonium chloride in 800 ml of dry methanol and, after half an hour, 60 g of acetophenone were added. That reaction solution was refluxed for 3 hours, after which the precipitated salt was filtered off at room temperature and the filtrate was evaporated down under reduced pressure. Separation from the triphenylphosphine oxide was effected by digesting the residue with petroleum ether (bp. 50°–70° C.) and the solution was evaporated down under reduced pressure.

The residue was taken up in 1 l of carbon tetrachloride, and the solution was refluxed with 81.7 g of N-bromosuccinimide and 4 g of 2,2′-azobisisobutyronitrile. When the reaction was complete, the succinimide was separated off by filtration, the filtrate was evaporated down under reduced pressure and the residue was recrystallized from methanol. 65.5 g (43%) of Z-1-(2-chlorophenyl)-2-phenyl-3-bromoprop-1-ene of the melting point 78° C. were obtained.

EXAMPLE B 30 g of Z-1-(2-chlorophenyl)-2-phenyl-3-bromoprop-1-ene were refluxed with 23 of 3-chloroperoxybenzoic acid in 500 ml of chloroform. When the reaction was complete, the chloroform phase was washed acid-free with aqueous sodium bicarbonate solution and water, dried over sodium sulfate and evaporated down under reduced pressure. The residue gave 41.3 g (70.2%) of 2-bromomethyl-2-phenyl-(2-chlorophenyl)-oxirane, which was then further processed with triazole according to the Example below. II. Preparation of the end products

EXAMPLE 1

23 g of 1,2,4-triazole and 5 g of sodium hydride (80% strength dispersion in mineral oil) were suspended in 150 ml of N,N-dimethylformamide, and a solution of 32 g of 2-bromomethyl-2-phenyl-3-(2-chlorophenyl)-oxirane in 150 ml of N,N-dimethylformamide was added at room temperature. After 8 hours, the reaction solution was poured onto water and extracted with ethyl acetate. The organic phase was washed with water and drid over sodium sulfate, and the solvent was evaporated off under reduced pressure. Recrystallization from diisopropyl ether gave 24 g of Z-2-(1,2,4-triazol-1-ylmethyl)-2-phenyl-3-(2-chlorophenyl)oxirane of melting point 150° C. (compound No. 1).

The compounds given in the table below may be prepared as in Example 1.

| No. | R | Hal | M.p. | Z | Isomer |
|---|---|---|---|---|---|
| 1 | $C_6H_5$ | Cl | 164–166° C. | N | Z |
| 2 | $4\text{-}ClC_6H_4$ | Cl | 166° C. | N | Z |
| 3 | 4-biphenyl | Cl | 191° C. | N | Z |
| 4 | $2,4\text{-}Cl_2\text{--}C_6H_3$ | Cl | | N | Z |
| 5 | $2\text{-}Cl\text{--}C_6H_4$ | Cl | | N | Z |
| 6 | $2\text{-}F\text{--}C_6H_4$ | Cl | | N | Z |
| 7 | $4\text{-}CH_3\text{--}C_6H_4$ | Cl | 140° C. | N | Z |
| 8 | $4\text{-}F\text{--}C_6H_4$ | Cl | 136° C. | N | Z |
| 9 | $3\text{-}Br\text{--}4\text{-}F\text{--}C_6H_3$ | Cl | 129–130° C. | N | Z |
| 10 | $4\text{-}Br\text{--}C_6H_4$ | Cl | | N | Z |
| 11 | $3,4\text{-}Cl_2\text{--}C_6H_3$ | Cl | | N | Z |
| 12 | $4\text{-}t\text{-}C_4H_9\text{--}C_6H_4$ | Cl | | N | Z |
| 13 | $3\text{-}Cl\text{--}C_6H_4$ | Cl | | N | Z |
| 14 | $3,5\text{-}Cl_2\text{--}C_6H_3$ | Cl | | N | Z |
| 15 | $p\text{-}C_6H_5\text{--}O\text{--}C_6H_4\text{--}$ | Cl | | N | Z |
| 16 | $4\text{-}Cl\text{--}C_6H_4$ | F | 138–140° C. | N | Z |
| 17 | $C_6H_5$ | F | 139° C. | N | Z |
| 18 | p-biphenyl | F | | N | Z |
| 19 | $2,4\text{-}Cl_2\text{--}C_6H_3$ | F | 117° C. | N | Z |
| 20 | $2\text{-}Cl\text{--}C_6H_4$ | F | | N | Z |
| 21 | $2\text{-}F\text{--}C_6H_4$ | F | 128° C. | N | Z |
| 22 | $4\text{-}CH_3\text{--}C_6H_4$ | F | 131° C. | N | Z |
| 23 | $4\text{-}F\text{--}C_6H_4$ | F | 114° C. | N | Z |
| 24 | $3\text{-}Br\text{--}4\text{-}F\text{--}C_6H_3$ | F | 106° C. | N | Z |
| 25 | $4\text{-}Br\text{--}C_6H_4$ | F | | N | Z |
| 26 | $3,4\text{-}Cl_2\text{--}C_6H_3$ | F | | N | Z |
| 27 | $4\text{-}t\text{-}C_4H_9\text{--}C_6H_4$ | F | | N | Z |
| 28 | $3\text{-}Cl\text{--}C_6H_4$ | F | | N | Z |
| 29 | $3,5\text{-}Cl_2\text{--}C_6H_3$ | F | | N | Z |
| 30 | $n\text{-}C_6H_5\text{--}O\text{--}C_6H_4$ | F | | N | Z |
| 31 | $4\text{-}Cl\text{--}C_6H_4$ | Br | | N | Z |
| 32 | $C_6H_5$ | Br | 153° C. | N | Z |
| 33 | p-biphenyl | Br | | N | Z |
| 34 | $2,4\text{-}Cl_2\text{--}C_6H_3$ | Br | | N | Z |
| 35 | $2\text{-}Cl\text{--}C_6H_4$ | Br | | N | Z |
| 36 | $2\text{-}F\text{--}C_6H_4$ | Br | | N | Z |
| 37 | $4\text{-}CH_3\text{--}C_6H_4$ | Br | | N | Z |
| 38 | $4\text{-}F\text{--}C_6H_4$ | Br | | N | Z |
| 39 | $3\text{-}Br\text{--}4\text{-}F\text{--}C_6H_4$ | Br | | N | Z |
| 40 | $4\text{-}Br\text{--}C_6H_4$ | Br | | N | Z |
| 41 | $3,4\text{-}Cl_2\text{--}C_6H_3$ | Br | | N | Z |
| 42 | $4\text{-}t\text{-}C_4H_9\text{--}C_6H_4$ | Br | | N | Z |
| 43 | $3\text{-}Cl\text{--}C_6H_4$ | Br | | N | Z |
| 44 | $3,5\text{-}Cl_2\text{--}C_6H_3$ | Br | | N | Z |
| 45 | $2\text{-}C_6H_5\text{--}O\text{--}C_6H_4$ | Br | | N | Z |
| 46 | $4\text{-}Cl\text{--}C_6H_5$ | Cl | 90–92° C. | CH | Z/E 70:30 |
| 47 | $C_6H_5$ | Cl | 85–87° C. | CH | Z/E 15:85 |
| 48 | $CH_3$ | Cl | 91° C. | N | Z |
| 49 | $CH_3$ | Cl | | CH | Z |
| 50 | $CH_3$ | F | | N | Z |
| 51 | $CH_3$ | F | | CH | Z |
| 52 | $CH_3$ | Br | | CH | Z |
| 53 | $CH_3$ | Br | | N | Z |
| 54 | $t\text{-}C_4H_9$ | F | | CH | Z |
| 55 | $t\text{-}C_4H_9$ | F | | N | Z |
| 56 | $t\text{-}C_4H_9$ | Cl | | CH | Z |
| 57 | $t\text{-}C_4H_9$ | Cl | | N | Z |
| 58 | $t\text{-}C_4H_9$ | Br | | CH | Z |
| 59 | $t\text{-}C_4H_9$ | Br | | N | Z |

In general terms, the novel compounds are very effective against a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, in particular wheat, rye, barley, oats, rice, corn, cotton, soybean, coffee, sugar cane, fruit and ornamentals in horiculture, in viticulture, and for vegetables, such as cucumbers, beans and Cucurbitaceae.

The novel compounds are particularly useful for controlling the following plant diseases:

*Erysiphe graminis* in cereals,
*Erysiphe cichoracearum* and *Sphaerotheca fuliginea* in Cucurbitaceae,
*Podosphaera leucotricha* in apples,
*Uncinula necator* in vines,
*Puccinia species* in cereals,
*Rhizoctonia solani* in cotton and lawns,
*Ustilago species* in cereals and sugar cane,
*Venturia inaequalis* (scab) in apples,
*Septoria nodorum* in wheat,
*Botrytis cinerea* (gray mold) in strawberries and vines,
*Cercospora arachidicola* in groundnuts,
*Pseudocercosporella herpotrichoides* in wheat and barley,
*Pyrenophora teres* in barley,
*Pseudocercosporella herpotrichoides* in wheat and barley,
*Pyricularia oryzae* in rice,
*Hemileia vastatrix* in coffee,
*Alternaria solani* in potatoes and tomotoes,
*Sclerotium rolfsii* in groundnuts and lawns, and
Fusarium and Verticillium species in various plants.

The compounds are applied by spraying or dusting plants with the active ingredients, or treating the seeds of the plants with the active ingredients. They are applied before or after infection of the plants or seeds by the fungi.

The novel substances can be converted to the conventional formulations, such as solutions, emulsions, suspensions, dusts, powders, pastes and granules. The forms for use depend entirely on the purposes for which they are intended; they should at all events ensure a fine and uniform distribution of the active substance. The formulations are produced in a known manner, for example by extending the active ingredient with solvents and/or carriers, with or without the use of emulsifiers and dispersants; if water is used as a diluent, it is also possible to employ other, organic solvents as auxiliary solvents. Suitable assistants for this purpose are essentially solvents, such as aromatics (eg. xylene or benzene), chlorinated aromatics (eg. chlorobenzenes), paraffins (eg. oil fractions), alcohols (eg. methanol or butanol), ketones (eg. cyclohexanone), amines (eg. ethanolamine or dimethylformamide) and water; carriers, such as ground natural minerals (kaolins, aluminas, talc or chalk) and ground synthetic minerals (eg. highly disperse silica or silicates); emulsifiers, such as nonionic and anionic emulsifiers (eg. polyoxyethylene fatty alcohol ethers, alkylsulfonates and arylsulfonates) and dispersants, such as lignin, sulfite waste liquors and methylcellulose.

The fungicides generally contain from 0.1 to 95, preferably from 0.5 to 90, % by weight of active ingredient.

The application rates are from 0.02 to 3 kg or more of active ingredient per ha, depending on the type of effect desired. The novel compounds may also be employed in material protection, inter alia for controlling wood-destroying fungi, such as *Coniophora puteana* and *Polystictus versicolor*. The novel active ingredients can also be used as fungicidal components of oily wood preservatives for protecting wood against wood-discoloring fungi. They are used by treating, for example impregnating or painting, the wood with these agents.

The agents and the ready-to-use formulations prepared from them, such as solution, emulsions, suspensions, powders, dusts, pastes or granules, are applied in a conventional manner, for example by spraying, atomizing, dusting, scattering, dressing or watering.

Examples of such formulations are:

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 8 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 17 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 8 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 17 is intimately mixed with 97 parts by weight of particulate kaolin. A dust is obtained containing 3% weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 2 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be present together with other active ingredients, for example herbicides, insecticides, growth regulators and fungicides, or may furthermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecylimidazol-2-yl acetate,
2,4-dichloro-6-(p-chloroanilino)-s-triazine,
0,0-diethyl phthalimidophosphonothioate,
5-amino-1-[bis-(dimethylamino)-phosphinyl]-3-phenyl-1,2,4-triazole,
2,3-dicyano-1,4-dithiaantraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin, 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)-butan-2-one,
1-( 1-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-2-dimethylamino-4-hydroxy-6-methylpyrimidine,
bis-(p-chlorophenyl-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3]3-(3,5-dimethyl-2-oxycyclohexyl)-2-hydroxethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[-(ethylaminocarbonyl)-2-methoximino]-acetimide,
1[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1((bis-(4-fluorophenyl)-methylsilyl)-methyl)-1H-1,2,4-triazole.

For the following experiments, the prior art active ingredient 2-(1,2,4-triazol-1-yl-methyl)-2-(4-chlorophenyl)-3-(2,4-dichlorophenyl)-oxirane (A) (EP 94,564) was used.

EXPERIMENT 1

Action on powdery mildew of wheat

Leaves of pot-grown wheat seedlings of the Frühgold variety were sprayed with aqueous spray liquor containing (dry basis) 80% of active ingredient and 20% of emulsifier, and, 24 hours after the spray coating had dried on, the leaves were dusted with oidia (spores) of powdery mildew of wheat (*Erysiphe graminis* var. tritici). The test plants were then placed in a greenhouse at from 20° to 22° C. and from 75 to 80% relative humidity. After 7 days, the extent of powdery mildew spread was determined.

The results show that, when used as a liquor containing the active ingredient in a concentration of 0.025, 0.006 or 0.0015 wt%, for example compounds 2, 8, 16, 21, 23 and 17 had a better fungicidal action (97%) than prior art compound A (90%).

EXPERIMENT 2

Action on wheat brown rust

Leaves of pot-grown wheat seedlings of the Frühgold variety were dusted with spores of brown rust (*Puccinia recondita*). The pots were then placed in a chamber at from 20° to 22° C. and with a high humidity (90–95%) for 24 hours. During this time, the spores germinated, and the germ tubes penetrated into the leaf tissue. The infected plants were then sprayed to runoff with aqueous spray liquors containing (dry basis) 80% of active ingredient and 20% of emulsifier. When the spray coating had dried on, the test plants were placed in a greenhouse at from 20° to 22° C. and from 65 to 70% relative humidity. After 8 days the extent of development of rust fungi on the leaves was determined.

The results show that, when used as a liquor containing the active ingredient in a concentration of 0.006 or 0.0015%, compounds 1, 2, 3, 7, 8, 9, 16, 23, 24 and 17 had a better fungicidal action (97%) than prior art compound A (70%).

EXPERIMENT 3

Action on *Pyrenophora teres*

Leaves of barley seedlings of the Asse variety, in the two-leaf stage, were sprayed to runoff with an aqueous spray liquor containing (dry basis) 80% of active ingredient and 20% of emulsifier. After 24 hours the plants were inoculated with a spore suspension of *Pyrenophora teres*, and cultivated further for 48 hours in a cabinet at 18° C. and a high relative humidity. The plants were then kept for a further 5 days in the greenhouse at 20° to 22° C. and 70% relative humidity. The spread of the symptoms was then assessed.

The results show that, when used as a liquor containing the active ingredient in a concentration of 0.05%, compounds 1, 2, 3, 16, 21, 24 and 8 have a good fungicidal action (97%).

We claim:

1. An azolylmethyloxirane of the formula

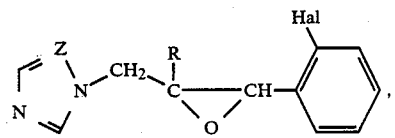

where R is $C_1$–$C_4$-alkyl, naphthyl, biphenyl or phenyl, and the phenyl radical may be substituted by halogen, nitro or phenoxy or by alkyl, alkoxy or haloalkyl, each of 1 to 4 carbon atoms, Hal is fluorine or chlorine and =Z— is =CH— or =N—, and its plant-tolerated addition salts with acids and metal salts.

2. A fungicidal composition comprising a fungicidally effective amount of an azolylmethyloxirane of the formula

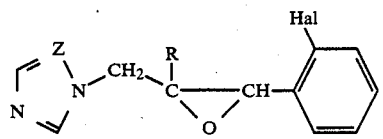

where R is $C_1$–$C_4$-alkyl, naphthyl, biphenyl or phenyl, and the phenyl radical may be substituted by halogen, nitro or phenoxy or by alkyl, alkoxy or haloalkyl, each of 1 to 4 carbon atoms, Hal is fluorine or chlorine and =Z— is =CH— or =N—, or a plant-tolerated acid addition or metal salt thereof, and an inert additive.

3. A process for combatting fungi, wherein a fungicidally effective amount of an azolylmethyloxirane of the formula

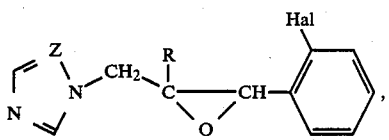

where R is $C_1$–$C_4$-alkyl, naphthyl, biphenyl or phenyl, and the phenyl radical may be substituted by halogen, nitro or phenoxy or by alkyl, alkoxy or haloalkyl, each of 1 to 4 carbon atoms, Hal is fluorine or chlorine and =Z— is =CH— or =N—, or a plant-tolerated acid addition or metal salt thereof, is allowed to act on the fungi or on materials, areas, plants or seed threatened by fungus attack.

4. A compound of the formula I as defined in claim 1, wherein R is 4—F—$C_6$—$H_4$, Hal is Cl and Z is N.

5. A compound of the formula I as defined in claim 1, wherein R is 4—Cl—$C_6$—$H_4$, Hal is F and Z is N.

6. A compound of the formula I as defined in claim 1, wherein R is phenyl, Hal is Cl and Z is N.

7. A compound of the formula I as defined in claim 1, wherein R is 4-chlorophenyl, Hal is Cl and Z is N.

* * * * *